United States Patent

Nagel

Patent Number: 5,971,920
Date of Patent: Oct. 26, 1999

[54] SURGICAL RETRACTOR

[76] Inventor: Gunther Peter Nagel, 427 W. Pueblo, Santa Barbara, Calif. 93105

[21] Appl. No.: 08/877,777

[22] Filed: Jun. 18, 1997

[51] Int. Cl.$^6$ .................................................. A61B 17/00
[52] U.S. Cl. ........................... 600/206; 600/210; 600/217
[58] Field of Search ................................. 600/201, 206, 600/210, 217, 240

[56] References Cited

U.S. PATENT DOCUMENTS

| | | | |
|---|---|---|---|
| 1,601,035 | 9/1926 | Nauth | 600/217 |
| 4,610,243 | 9/1986 | Ray | 600/217 X |
| 4,616,633 | 10/1986 | Vargas Garcia . | |
| 4,616,635 | 10/1986 | Caspar et al. | 600/217 X |
| 4,621,619 | 11/1986 | Sharpe | 600/217 |
| 4,995,875 | 2/1991 | Coes | 600/210 X |
| 5,052,373 | 10/1991 | Michelson | 600/217 |
| 5,743,853 | 4/1998 | Lauderdale | 600/210 |

*Primary Examiner*—Jeffrey A. Smith
*Attorney, Agent, or Firm*—Daniel R. Kimbell

[57] ABSTRACT

A surgical retractor, particularly suitable for soft tissue surgery such as plastic surgical procedures. The retractor has an elongate planar portion with a proximal end and a distal end, a main body portion therebetween, an upper surface and a bottom surface. The distal end of the retractor has a generally semi-circular shape, and has teeth extending from the perimeter thereof which extend above the upper surface of the retractor. The plurality of teeth are generally triangular in shape with apexes extending upwardly from the plane of the upper surface of the retractor and the teeth are smooth along their edges and apexes. The retractor is formed of generally rigid, yet malleable material, such as metal or plastic.

9 Claims, 1 Drawing Sheet

SURGICAL RETRACTOR

TECHNICAL FIELD OF THE INVENTION

The invention relates to the field of surgical instruments, particularly to retractors used in soft tissue surgery, such as in performing plastic surgery and other surgeries.

BACKGROUND OF THE INVENTION

In surgery, the ability to gain access to, and maintain clear access in the surgical field is very important. Surgical retractors are commonly used to lift and move tissue to allow a variety of surgical activities, such as cutting, sewing, stemming blood flow, and other activities to take place in the surgical field. The problems in dealing with the retraction of soft tissue are two fold. First, since the tissue is soft, there is a tendency for the tissue to flop down around the retractor. Second, since most retractors are relative smooth, slippage of the tissue often thereon can take place, requiring the surgeon and assistants to interrupt what they are doing, and reposition the retractor. These problems interfere with gaining and maintaining a clear surgical field.

There are many types of surgical retractors, some of which are discussed. U.S. Pat. No. 4,610,243 to Ray discloses a malleable force-fulcrum retractor which has a claw-like spike or spikes at a distal end which is used to penetrate the surface of a bone within an incision. The retractor can be bent to a desired shape before use, and by contacting the distal spike or spikes with bone, the middle of the retractor can be used to pry up tissue adjacent to the bone.

U.S. Pat. No. 4,616,633 to Vargas Garcia discloses a retractor for use in maxillofacial surgery. It has a palm engaging lesser blade portion and a greater active blade. Both blades extend from a central, straight handle section for manual grasping and manipulation. The greater blade extends at an adjustable angle from the handle section. Roughened surfaces are formed on its inside surfaces of the ends of both blades which are placed in contact with the tissue to be retracted. The distal ends of both blades, however, are straight and flat, and the overall shape of the device is not particularly well suited for use in lifting and retracting tissue during surgical procedures, where the ability to access various portions of tissue, and from different angles can be important.

U.S. Pat. No. 5,052,373 to Michelson discloses a spinal retractor having a pair of blades adjustably mounted on a frame. The blades have a saw-toothed pattern formed along the straight, outwardly flared distal ends of the blades, and are adapted to pry apart the muscle and other tissue adjacent the spine to clear a surgical field.

U.S. Pat. No. 4,621,619 to Sharpe discloses a retractor having an adhesive pad at a proximal end for attachment to a patient's skin, an arched middle portion, and a distal end having a pair of hooks facing the proximal end. Once positioned, the retractor is adapted not to be moved.

While the prior art discloses surgical refractors and other devices which include teeth or roughed surfaces at their distal ends, none teach or suggest a retractor particular well-suited for use in retraction of soft tissue during surgery, where the ability to access the tissue from a variety of angles, without the retracted tissue slipping off of the retractor, yet without causing any damage to the tissue is paramount. There accordingly remains a need for an improved surgical retractor particularly well suitable for use in soft tissue surgery.

SUMMARY OF THE INVENTION

In one aspect of the invention, a surgical retractor with a distal end having a plurality of protrusions is taught.

In another aspect of the invention, a surgical retractor having a planar, semicircular distal end, with teeth protruding generally perpendicularly therefrom is disclosed.

In yet another aspect of the invention, a surgical retractor being formed of malleable material, such as plastic or metal, is provided, so that the surgeon can change the shape of the retractor and thus provide for better access to the surgical field and over control of the tissue being retracted.

DETAILED DESCRIPTION OF THE INVENTION

Figure 1:
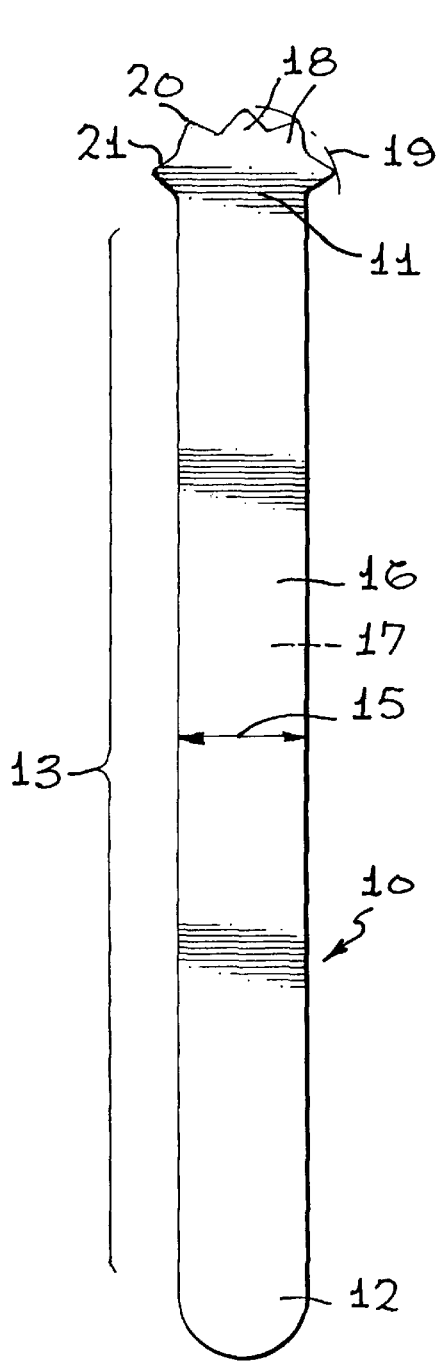
FIG. 1 is a plan view of an embodiment of the retractor, shown in a partially manufactured state, with its teeth splayed out from the plane of the retractor's head.
Figure 2:
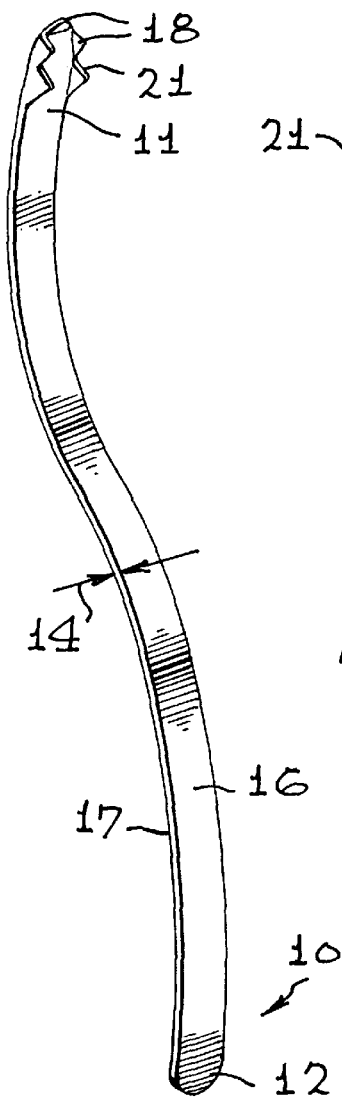
FIG. 2 is a front right-side perspective view of the retractor of FIG. 1, with the teeth positioned to extend upwardly from the plane of the retractor's head, and with the bar portion bent.
Figure 3:
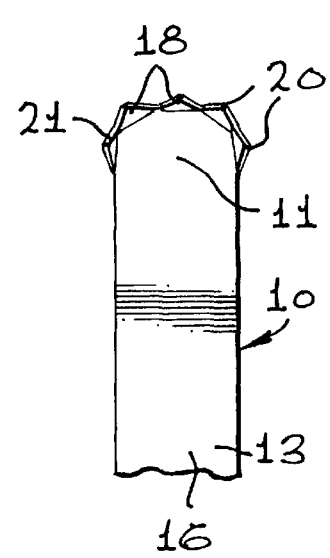
FIG. 3 is a top plan detail view showing the retractor's head.

Referring to FIGS. 1–3, retractor 10 of the invention is shown. Retractor 10 has an elongate planar shape with a distal end 11 and a proximal end 12 and a main body portion 13 located therebetween. Retractor 10 has a thickness 14 and a width 15 and an upper surface 16 and a lower surface 17. Referring to FIG. 1, a plurality of protrusions, or teeth 18 are formed at the distal end 11 of retractor 10, and extend outwardly from a generally semi-circular contour 19 of distal end 11. Teeth 18 preferably have a generally triangular shape, with the apexes 20 of teeth 18 extending outwardly from the generally semi-circular contour 19. Teeth 18 are preferably relatively smooth along the apexes 20 and along edges 21 thereof. The generally semi-circular contour 19 of the distal end 11 preferably has a diameter which is generally the same as the width 15 of the retractor so that distal end 11 of the retractor 10 remains compact in size and maneuverable in the generally tight space of surgical fields.

Retractor 10 is preferably formed of a generally rigid material, such as surgical stainless steel. At the same time or after being stamped from stainless steel plate, teeth 18 are bent upwardly to extend above upper surface 16 of retractor 10, as best shown in FIGS. 2 and 3. The mate rial used to form retractor 10 is also preferably somewhat malleable, such as appropriate surgical stainless steel, so that a surgeon may bend main body portion 13 of retractor 10 to best suit the needs of the surgical field. If desired, retractor 10 can be formed of other material, such as generally rigid, yet malleable aluminum, plastics, or other known materials.

Formed as such, distal end 11 will maintain a smooth and semi-circular contour 16, which smooth and semi-circular contour can be inserted between layers of tissue without unduly snagging or catching on tissue. The lower surface 17 of retractor 10 is smooth, and when inserted between layers of tissue will therefore not cause damage to underlying tissue. By lifting up on main body portion 13 of retractor, distal end 11 of retractor 10 with teeth 18 will lift up overlying tissue. Teeth 18 will prevent slippage of the tissue and allow the tissue to be lifted and moved, yet will reduce trauma to the tissue being lifted. The semi-circular shaped distal end 11 of the retractor 10 allows the retractor 10 to be inserted at a variety of angles relative to the plane of the overlying tissue, and permits the surgeon to easily lift, support, and manipulate tissue from the variety of angles of approach.

The drawings and the foregoing description are not intended to represent the only form of the invention in regard to the details of this construction and manner of operation. In fact, it will be evident to one skilled in the art that modifications and variations may be made without departing from the spirit and scope of the invention. Although specific terms have been employed, they are intended in a generic and descriptive sense only and not for the purpose of limitation, the scope of the invention being delineated in the following the claims which follow.

I claim:

1. A surgical retractor, consisting of:

an elongate planar portion with a proximal end and a distal end, a main body portion therebetween, and an upper surface and a lower surface, wherein the distal end of the retractor has a generally semi-circular shape and has a plurality of protrusions comprising teeth which extend generally upwardly around a perimeter of the generally semi-circular shaped distal end.

2. The surgical retractor of claim 1, wherein the plurality of protrusions are generally triangular in shape with apexes extending upwardly from the plane of the upper surface of the retractor.

3. The surgical retractor of claim 1, wherein the plurality of teeth have smooth edges.

4. The surgical retractor of claim 1, wherein the retractor is formed from generally rigid, yet malleable material.

5. The surgical retractor of claim 1, wherein the retractor is formed from generally rigid, yet malleable stainless steel.

6. A surgical retractor, particularly suitable for soft tissue surgery, comprising:

an elongate planar portion with a proximal end and a distal end, a main body portion therebetween, an upper surface and a lower surface, wherein the distal end of the retractor has a generally semi-circular shape, and has a plurality of teeth extending from a perimeter of the generally semi-circular distal end and extending above the upper surface of the retractor.

7. The retractor of claim 6, wherein the plurality of teeth are generally triangular in shape with apexes extending upwardly from a plane of the upper surface of the retractor, and wherein the plurality of teeth have smooth edges and apexes.

8. The retractor of claim 6, wherein the retractor is formed from generally rigid, yet malleable material, selected from metal and plastics.

9. The surgical retractor of claim 6, wherein the retractor is formed from generally rigid, yet malleable stainless steel.

* * * * *